(12) United States Patent
Gutierrez et al.

(10) Patent No.: US 10,160,802 B2
(45) Date of Patent: Dec. 25, 2018

(54) ANTI-MALARIAL COMPOSITIONS

(71) Applicants: Leidos, Inc., Reston, VA (US); The United States of America, as represented by the Secretary, Dept. of Health and Human Services, Washington, DC (US)

(72) Inventors: Gabriel M. Gutierrez, Reston, VA (US); James Pannucci, Reston, VA (US); Amy Noe, Reston, VA (US); Steve Chienwen Huang, Reston, VA (US); Scott Winram, Reston, VA (US); Annie Xiaoyan Mo, Bethesda, MD (US)

(73) Assignees: LEIDOS, INC., Reston, VA (US); THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 178 days.

(21) Appl. No.: 15/056,458

(22) Filed: Feb. 29, 2016

(65) Prior Publication Data
US 2016/0176955 A1 Jun. 23, 2016

Related U.S. Application Data

(62) Division of application No. 14/097,799, filed on Dec. 5, 2013, now Pat. No. 9,321,834.

(51) Int. Cl.
*A61K 39/015* (2006.01)
*C07H 21/02* (2006.01)
*A61K 39/02* (2006.01)
*C07K 16/20* (2006.01)
*A61K 39/395* (2006.01)
*A61K 45/06* (2006.01)
*A61K 39/00* (2006.01)

(52) U.S. Cl.
CPC .......... *C07K 16/205* (2013.01); *A61K 39/015* (2013.01); *A61K 39/39575* (2013.01); *A61K 45/06* (2013.01); *A61K 2039/505* (2013.01); *C07K 2317/24* (2013.01); *C07K 2317/33* (2013.01); *C07K 2317/34* (2013.01); *C07K 2317/565* (2013.01); *C07K 2317/622* (2013.01); *C07K 2317/76* (2013.01); *Y02A 50/412* (2018.01)

(58) Field of Classification Search
CPC .............................. A61K 39/00; A61K 39/395
USPC .......... 424/130.1, 133.1, 141.1, 150.1, 272.1
See application file for complete search history.

(56) References Cited

U.S. PATENT DOCUMENTS

| 6,080,588 | A | * | 6/2000 | Glick ................. A61K 31/5513 424/140.1 |
|---|---|---|---|---|
| 8,530,171 | B2 | | 9/2013 | Retallack et al. |
| 2005/0208020 | A1 | | 9/2005 | Doolan et al. |
| 2006/0122266 | A1 | | 6/2006 | Sinnis et al. |
| 2006/0127413 | A1 | | 6/2006 | Sutter et al. |
| 2006/0188527 | A1 | | 8/2006 | Hoffman et al. |
| 2008/0131461 | A1 | | 6/2008 | Pau et al. |
| 2008/0213318 | A1 | | 9/2008 | Clements et al. |
| 2009/0092619 | A1 | | 4/2009 | Sinnis et al. |
| 2009/0285879 | A1 | | 11/2009 | Pau et al. |
| 2010/0113609 | A1 | | 5/2010 | Sinnis et al. |
| 2010/0183590 | A1 | | 7/2010 | Druilhe et al. |
| 2010/0255018 | A1 | | 10/2010 | Deloron et al. |
| 2011/0008383 | A1 | | 1/2011 | Powell et al. |
| 2011/0033502 | A1 | | 2/2011 | Kappe et al. |
| 2011/0223179 | A1 | | 9/2011 | Sinnis et al. |
| 2011/0287443 | A1 | | 11/2011 | Retallack et al. |
| 2012/0014994 | A1 | | 1/2012 | Pau et al. |
| 2012/0301472 | A1 | * | 11/2012 | Tedder ............. A61K 39/39533 424/136.1 |
| 2013/0022612 | A1 | | 1/2013 | Sinnis et al. |
| 2013/0129767 | A1 | | 5/2013 | Tuikue Ndam et al. |

FOREIGN PATENT DOCUMENTS

| WO | 199217204 A1 | 10/1992 |
|---|---|---|
| WO | 2005063805 A1 | 7/2005 |
| WO | 2011123139 A1 | 10/2011 |
| WO | 2011126811 A2 | 10/2011 |

OTHER PUBLICATIONS

Aldrich et al., "Roles of the Amino Terminal Region and Repeat Region of the Plasmodium berghei Circumsporozoite Protein in Parasite Infectivity," PLoS ONE, Feb. 2012, vol. 7, Issue 2, pp. 1-12.
Aley et al., "Synthetic peptides from the circumsporozoite proteins of Plasmodium falciparum and Plasmodium knowlesi recognize the human hepatoma cell line HepG2-A16 in vitro," Journal of Experimental Medicine, vol. 164, No. 6, Dec. 1, 1986, pp. 1915-1922.
Arévalo-Herrera et al., "Mapping and comparison of the B-cell epitopes recognized on the Plasmodium vivax aircumsporozoite protein by immune Colombians and immunized Aotus monkeys," Abstract, Ann Trop. Med. Parasitol, 1998, vol. 92, No. 5, pp. 539-551.
Bongfen et al., "The N-terminal domain of Plasmodium falciparum circumsporozoite protein represents a target of protective immunity," Abstract, Vaccine, 2009, vol. 27, No. 2, pp. 328-335.
Coppi et al., "The malaria circumsporozoite protein has two functional domains, each with distinct roles as sporozoites journey from mosquito to mammalian host," J. Exp. Med., 2011, vol. 208, No. 2, pp. 341-356.

(Continued)

*Primary Examiner* — Rodney P Swartz
(74) *Attorney, Agent, or Firm* — Banner & Witcoff, Ltd.

(57) ABSTRACT

This disclosure provides antibodies that are useful for preventing and/or treating malaria. The epitope to which the antibodies bind is in close proximity to the conserved proteolytic cleavage site of *P. falciparum* circumsporozoite protein (CSP), and the antibodies provided in this disclosure can prevent cleavage and inhibit *P. falciparum* sporozoites from invading the liver.

7 Claims, 7 Drawing Sheets

Specification includes a Sequence Listing.

(56) References Cited

OTHER PUBLICATIONS

Coppi et al., "The Plasmodium circumsporozoite protein is proteolytically processed during cell invasion," Journal of Experimental Medicine, vol. 201, No. 1, Jan. 3, 2005, pp. 27-33.
de la Cruz et al., "Sequence Variation in Putative Functional Domains of the Circumsporozoite Protein of Plasmodium falciparum," The Journal of Biological Chemistry, vol. 262, No. 25, Sep. 5, 1987, pp. 11935-11939.
Delgado et al., "Dynamics of Anti PvCSP-Antibodies During the First 28-Days Follow Up After Radical Cure Treatment in the Peruvian Amazon," Advances in Plasmodium vivax Malaria Research, Poster Sessions, May 28-29, 2013, p. 1 and p. 13.
Doolan et al., HLA-DR-Promiscuous T Cell Epitopes from Plasmodium falciparum Pre-Erythrocytic-Stage Antigens Restricted by Multiple HLA Class II Alleles 1,2.
Doud et al., "Unexpected fold in the circumsporozoite protein target of malaria vaccines," PNAS, May 15, 2012, vol. 109, No. 20, pp. 7817-7822.
International Search Report and Written Opinion for PCT/US14/68731, dated Mar. 26, 2015.
Jalloh et al., "T-cell epitope polymorphisms of the Plasmodium falciparum circumsporozoite protein among field isolates from Sierra Leone: age-dependent haplotype distribution?," Malarial Journal, 2009, vol. 8, No. 120, pp. 1-9.
Mata et al., "Malaria Vaccine Adjuvants: Latest Update and Challenges in Preclinical and Clinical Research," Hindawi Publishing Corporation, vol. 2013, Article ID 282913, pp. 1-19.
McIntosh et al., "The Importance of Human FcgRI in Mediating Protection to Malaria," PLoS Pathogens, May 2007, vol. 3, Issue 5, e72, pp. 0647-0658.
Pleass & Holder, "Opinion: antibody-based therapies for malaria," Abstract, Nat. Rev. Microbiol., 2005, vol. 3, No. 11, pp. 893-899.
Rathore et al., "An Immunologically Cryptic Epitope of Plasmodium falciparum Circumsporozoite Protein Facilitates Liver Cell Recognition and Induces Protective Antibodies That Block Liver Cell Invasion," The Journal of Biological Chemistry, 2005, vol. 280, No. 21, Issue of May 27, pp. 20524-20529.
Sedegah et al., "Identification of minimal human MHC-restricted CD8+ T-cell epitopes within the Plasmodium falciparum circumsporozoite protein (CSP)," Malaria Journal, 2013, vol. 12, No. 185, pp. 1-17.
Yadava et al., "Cross-Species Immunity Following Immunization With a Circumsporozoite Protein-Based Vaccine for Malaria," The Journal of Infectious Diseases, 2012, pp. 1-8.
Ying et al., "The Malaria Circumsporozoite Protein: Interaction of the Conserved Regions I and II-Plus with Heparin-like Oligosaccharides in Heparan Sulfate," Experimental Parasitology, vol. 85, No. 2, Feb. 1, 1997, pp. 168-182.
Zeeshan et al., "Genetic variation in the Plasmodium falciparum Circumsporozoite Protein in India and its Relevance to RTS,S Malaria Vaccine," PLoS One, Aug. 2012, vol. 7, Issue 8, e43430, pp. 1-10.
Zevering et al., "Major population differences in T cell response to a malaria sporozoite vaccine candidate," Abstract, Int. Immunol., 1990, vol. 2, No. 10, pp. 945-955.
Persson et al., "Cutting Edge: a New Tool to Evaluate Human Pre-Erythrocytic Malaria Vaccines: Rodent Parasites Bearing a Hybrid Plasmodium falciparum Circumsporozoite Protein," J. Immunol. 169, 6681-85 2002.

* cited by examiner

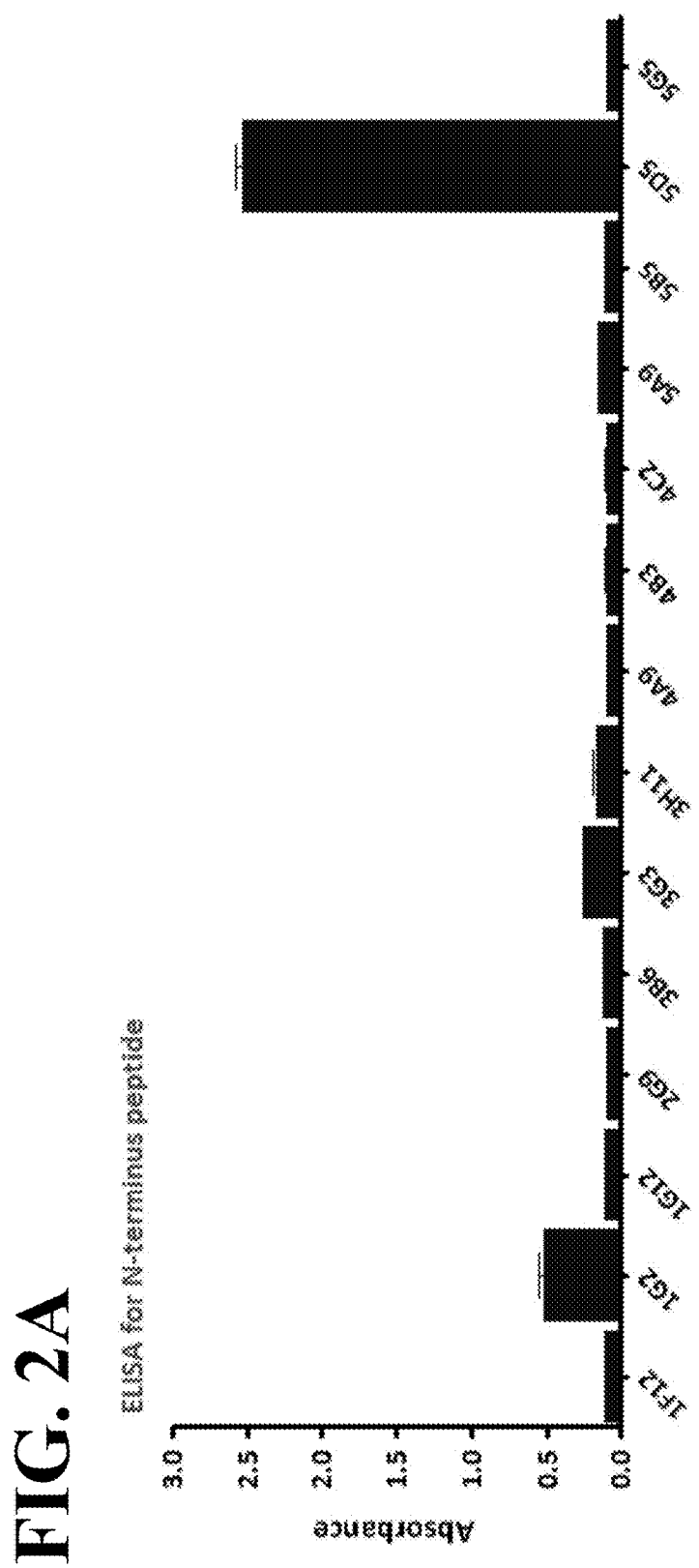

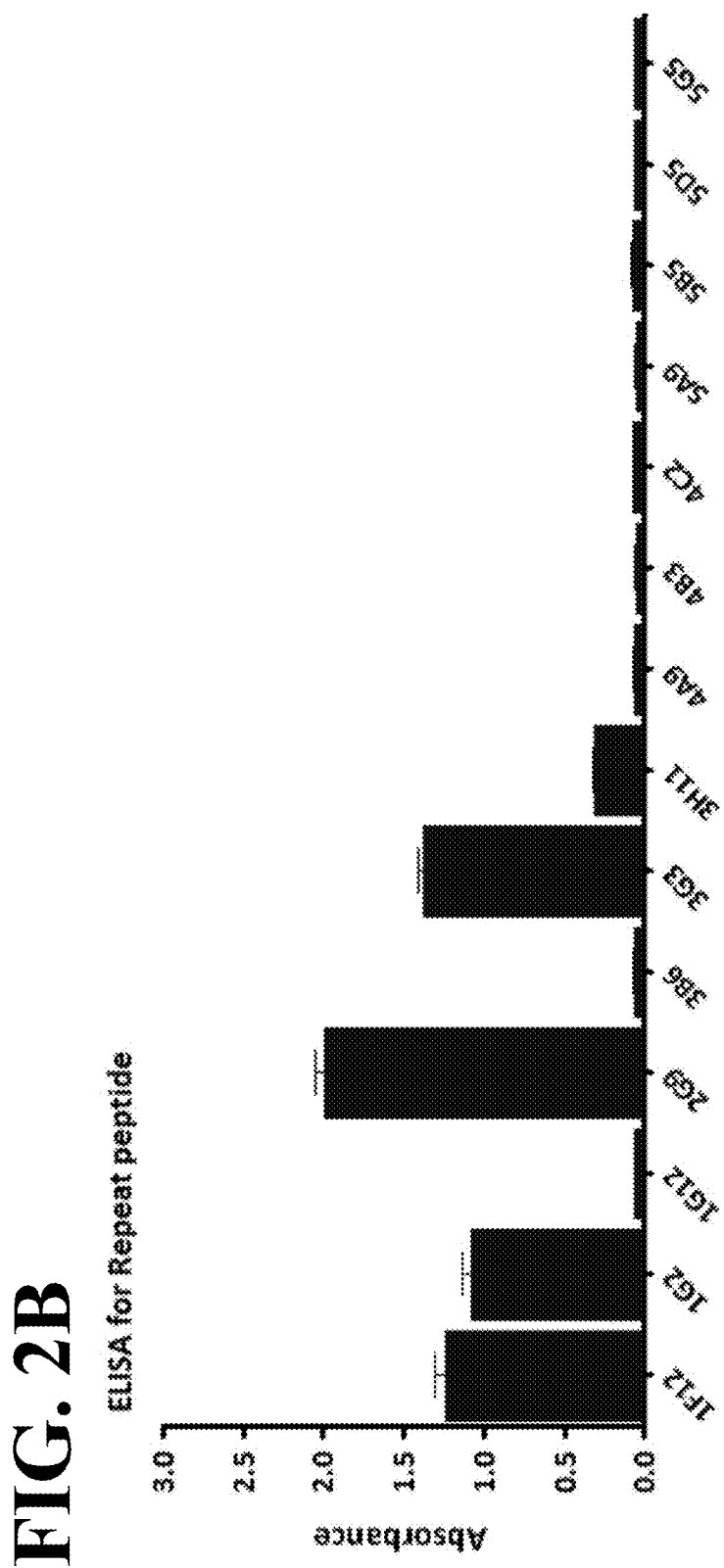

FIG. 6A

5D5 Heavy Chain

```
         <--Signal Sequence-><----------H1-------  ------->< --CDR1
   1     MEWIWIFLFI LSGTAGVQSQ VHLQQSGGEV ARPGASVKLS CKASGYTFTG ---><----H2-------><------CDR2----------><-----H3--
  51     YGLSWVKQRT GQGLEWIGEI YPRSGNTYYN EKFKGKATLT ADKSSSTAYM --------H3--------><--CDR3--->-DJ Joint--><------CH1----
 101     ELRSLTSEDS AVYFCARSWG NSSFVYWGQG TLVTVSAAKT TPPSVYPLAP

------------CH1---------------->
 151     GSAAQTNSMV TLGCLVKGYF PEPVTVTWN
```

FIG. 6B

5D5 Kappa Chain

```
         ----Signal Peptide---><-----Framework 1---------><CDR1-L1
   1     MKSQTQVFVF LLLCVSGAHG SIVMTQTPKF LLVSAGDRVT ITCKASQSVT ---><-----Framework 2-><--CDR2-><----
  51     NDVTWYQQKP GQSPKLLIYY ASNRYTGVPD RFTGSGYGTD FTFTISTVQA -FW3---><-CRR3---><---Joint---><--------Kappa Constant-
 101     EDLAVYFCQQ DYSSPFTFGS GTKLEIKRAD AAPTVSIFPP SSEQLSNSCS
```

ANTI-MALARIAL COMPOSITIONS

This application incorporates by reference the contents of a 11.4 kb text file created on Feb. 25, 2016 and named "00047900245 sequencelisting.txt," which is the sequence listing for this application.

Each reference cited in this disclosure is incorporated herein by reference in its entirety.

TECHNICAL FIELD

The invention relates to compositions and methods for preventing and treating malaria.

BRIEF DESCRIPTION OF THE DRAWINGS

FIGS. 2A-B. Graphs demonstrating binding of anti-CSP mAbs to regions of P. falciparum CSP by ELISA. FIG. 2A shows binding of mAb 5D5 strongly to a long CSP N-terminal region peptide ("N-terminus peptide"). FIG. 2B shows binding of mAb 2G9 to a long CSP repeat region peptide ("Repeat peptide"). See Example 3.

FIG. 4A, schematic representation of P. falciparum CSP. FIG. 4B, peptides located in the N terminal region of CSP. Peptide 8, SEQ ID NO:17; peptide 9, SEQ ID NO:18; peptide 10, SEQ ID NO: 19. FIG. 4C, graph of results of peptide mapping by ELISA. See Example 5.

FIGS. 6A-B. Amino acid sequences of the heavy and light chain variable regions of mAb 5D5. CDR sequences are underlined. FIG. 6A, heavy chain variable region (SEQ ID NO:14). FIG. 6B, kappa (light) chain variable region (SEQ ID NO:16). See Example 7.

DETAILED DESCRIPTION

Figure 1:
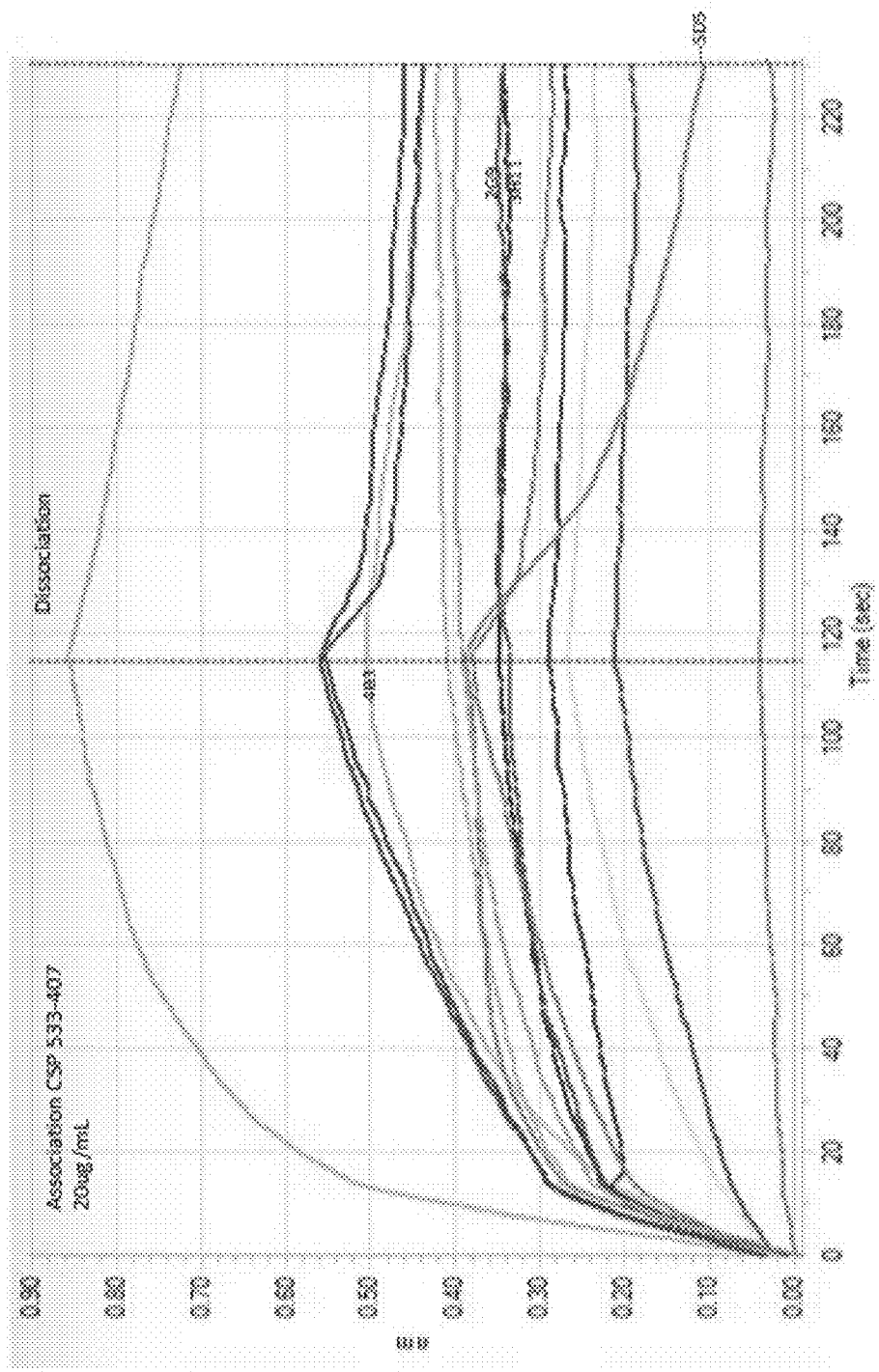
FIG. 1. Graph of results of biolayer interference assay (BLI) to detect binding of 14 monoclonal antibodies (mAbs) raised against recombinant circumsporozoite protein ("CSP"). Each line represents an individual antibody, and the lines representing antibodies 4B3, 2G9, 3H11, and 5D5 are indicated. See Example 2.

Malaria is an infectious, febrile disease which is caused by protozoa of the genus *Plasmodium*. Malaria is transmitted by the bites of infected *Anopheles* mosquitoes and can be caused by any *Plasmodium* species that infects humans, including, but not limited to, *Plasmodium vivax* and *Plasmodium falciparum*.

Circumsporozoite protein (CSP) is the major protein on the surface of the *Plasmodium* sporozoite. CSP contains an N-terminal domain, a conserved pentapeptide protease cleavage site at the core of region I, a repeat region, a short conserved sequence termed region III, and a C-terminal region with sequence homology to the thrombospondin type-1 repeat superfamily (Dowd et al., *Proc. Natl. Acad. Sci. USA* 109, 7817-22, 2012). CSP is proteolytically processed cysteine protease during invasion of hepatocytes (Coppi et al., *J. Exp. Med.* 201, 27-33, 2005). Processing occurs on the sporozoite surface when sporozoites contact hepatocytes, resulting in the removal of the amino-terminal third of the protein. The cleavage site is a five amino acid sequence (KLKQP; SEQ ID NO:20), which is highly conserved among *P. falciparum* isotypes.

This disclosure provides antibodies that bind to an epitope in close proximity to the protease cleavage site of CSP. Binding of the antibodies to this epitope can prevent cleavage and inhibit *Plasmodium* sporozoites from invading the liver. Because the cleavage site among all species of *Plasmodium* that infect humans is conserved, the disclosed antibodies can be used to treat or reduce infection in human by all such *Plasmodium* species.

5D5 Antibodies

Unless otherwise indicated, the term "antibody" means an intact antibody (e.g., an intact monoclonal antibody) or antigen-binding fragment of an antibody (e.g., an antigen-binding fragment of a monoclonal antibody), including intact antibodies or antigen-binding fragments that have been modified or engineered. Modified or engineered antibodies include, but are not limited to, chimeric antibodies, humanized antibodies, and multispecific antibodies (e.g., bispecific antibodies). Examples of antigen-binding fragments include Fab, Fab', F(ab')$_2$, Fv, single chain antibodies (e.g., scFv), and diabodies. Particularly useful subclasses of antibodies include IgG$_1$, IgG$_3$, and IgA.

A "5D5 antibody" is an antibody containing the CDR regions of monoclonal antibody (mAb) 5D5, which is described in the specific examples, below. The antibody mAb 5D5 was deposited on Nov. 19, 2013 with The Malaria Research and Reference Reagent Resource Center (MR4), which is managed by BEI Resources, which is managed by ATCC, under Accession No. MRA-1242. Availability of the deposited antibody is not to be construed as a license to use the antibody in contravention of the rights granted under the authority of any government in accordance with its patent laws. mAb 5D5 is a murine IgG$_1$/κ subclass antibody obtained using the full length recombinant CSP of *Plasmodium falciparum* (3D7 strain) as an immunogen.

The immunoglobulin heavy chain of mAb 5D5 antibody comprises CDR$_{H1}$ (GYTFTGYGLS; SEQ ID NO:1), CDR$_{H2}$ (IYPRSGNTYYNEKFKGKAT; SEQ ID NO:2), and CDR$_{H3}$ (SWGNSSFVY; SEQ ID NO:3). The immunoglobulin light chain variable region of mAb 5D5 comprises CDR$_{L1}$ (KASQSVTNDVT; SEQ ID NO:4), CDR$_{L2}$ (ASN-RYTG; SEQ ID NO:5), and CDR$_{L3}$ (QQDYSSPFT; SEQ ID NO:6). Together, these CDR regions define a binding site for the mAb 5D5 epitope EKLRKPKHKKLK (SEQ ID NO:7).

The locations of the mAb 5D5 epitope (bold and underlined) and the protease cleavage site (bold and italicized) within *P. falciparum* CSP (SEQ ID NO:8) are shown below:

MMRKLAILSVSSFLFVEALFQEYQCYGSSSNTRVLNELNYDNAGTNL

YNELEMNYYGKQENWYSLKKNSRSLGENDDGNNEDEKLRKPKHKKL

KQPADGNPDPNANPNVDPNANPNVDPNANPNVDPNANPNANPNANPN

ANPNANPNANPNANPNANPNANPNANPNANPNANPNANPNANPNANP

NANPNANPNVDPNANPNANPNANPNANPNANPNANPNANPNANPNAN

PNANPNANPNANPNANPNANPNANPNANPNANPNANPNKNNQGNGQG

```
-continued
HNMPNDPNRNVDENANANSAVKNNNNEEPSDKHIKEYLNKIQNSLST

EWSPCSVTCGNGIQVRIKPGSANKPKDELDYANDIEKKICKMEKCSS

VFNVVNSSIGLIMVLSFLFLN
```

In some variations, a 5D5 antibody is an scFv. Particularly useful 5D5 scFv antibodies are those which comprise an Fc region of the $IgG_1$, $IgG_3$, or IgA subclass.

In some variations, the CDR sequences of a 5D5 antibody are interposed between human or humanized immunoglobulin framework regions to reduce or eliminate antigenicity when administered to humans. Methods for humanizing antibodies are known in the art. For example, mouse immunoglobulin constant regions can be replaced with human immunoglobulin constant regions, as described in Morrison et al., *Proc. Natl. Acad. Sci. USA* 81, 6851-55, 1984; Neuberger et al., *Nature* 312, 604-08, 1984; U.S. Pat. No. 6,893,625; U.S. Pat. No. 5,500,362; and U.S. Pat. No. 4,816,567.

Alternatively, CDRs can be grafted into human framework regions. The human framework regions can be consensus human framework regions, created by aligning framework regions from several human heavy chain or light chain amino acid sequences to identify a consensus amino acid sequence. Descriptions of CDR grafting are provided, for example, in U.S. Pat. No. 7,022,500; U.S. Pat. No. 6,982,321; U.S. Pat. No. 6,180,370; U.S. Pat. No. 6,054,297; U.S. Pat. No. 5,693,762; U.S. Pat. No. 5,859,205; U.S. Pat. No. 5,693,761; U.S. Pat. No. 5,565,332; U.S. Pat. No. 5,585,089; U.S. Pat. No. 5,530,101; Jones et al., *Nature* 321, 522-25, 1986; Riechmann et al., *Nature* 332, 323-27, 1988; Verhoeyen et al., *Science* 239, 1534-36, 1988; and Winter, *FEBS Lett.* 430, 92-94, 1998.

Other approaches include SUPERHUMANIZATION™, in which human CDR sequences which are structurally similar to a mouse antibody can be chosen from human germline genes (e.g., U.S. Pat. No. 6,881,557; Tan et al., *J. Immunol.* 169, 1119-25, 2002); "reshaping," "hyperchimerization," or "veneering/resurfacing" (see, e.g., Vaswami et al., *Annals of Allergy, Asthma, & Immunol.* 81, 105 (1998); Roguska et al., *Prot. Engineer.* 9, 895-904 (1996); U.S. Pat. No. 5,639,641; U.S. Pat. No. 6,072,035); ACTIVMAB™ technology (Vaccinex, Inc., Rochester, N.Y.), which involves using a vaccinia virus-based vector to express antibodies in mammalian cells, producing high levels of combinatorial diversity of IgG heavy and light chains (e.g., U.S. Pat. No. 6,706,477; U.S. Pat. No. 6,800,442; and U.S. Pat. No. 6,872,518); and HUMAN ENGINEERING™ technology (XOMA (US) LLC (e.g., WO 93/11794; U.S. Pat. No. 5,766,886; U.S. Pat. No. 5,770,196; U.S. Pat. No. 5,821,123; and U.S. Pat. No. 5,869,619).

Production of 5D5 Antibodies

Methods for recombinant production of antibodies are well known in the art. For example, DNA molecules encoding light chain variable regions and heavy chain variable regions can be chemically synthesized using the amino acid sequence information provided in this disclosure. Synthetic DNA molecules can be ligated to other appropriate nucleotide sequences, including, e.g., constant region coding sequences and expression control sequences, to produce conventional gene expression constructs encoding the desired antibody. Production of gene expression constructs is within routine skill in the art. Nucleic acid molecules may comprise coding sequences for one or more of the CDRs of a 5D5 antibody. This disclosure provides the amino acid sequences of the CDRs, and any nucleotide sequence that encodes the desired amino acid sequence may be used to express the desired amino acid sequence. Non-limiting examples of nucleotide sequences include SEQ ID NO:13 (encoding the $V_H$ region of mAb 5D5) and SEQ ID NO:15 (encoding the $V_L$ region of mAb 5D5).

Nucleic acid molecules can encode one or more of the 5D5 CDRs. In some variations, a nucleic acid molecule encoding one or more of the 5D5 CDR sequences is a cDNA molecule having no introns.

Expression constructs expressing one or more of the 5D5 CDRs can be introduced into host cells through conventional transfection or transformation techniques. Examples of host cells are *E. coli* cells, Chinese hamster ovary (CHO) cells, HeLa cells, baby hamster kidney (BHK) cells, monkey kidney cells (COS), human hepatocellular carcinoma cells (e.g., Hep G2), and myeloma cells that do not otherwise produce immunoglobulins. Transformed host cells can be grown under conditions that permit the host cells to express the genes that encode the immunoglobulin light or heavy chain variable regions.

Alternatively, amino acid sequences of a 5D5 antibody can be synthesized using a peptide synthesizer, as is known in the art.

Pharmaceutical Compositions and Methods of Use

Pharmaceutical compositions comprising one or more of the 5D5 antibodies disclosed herein typically contain a sufficient concentration of 5D5 antibodies to reduce or prevent cleavage of CSP so that the invasion of the liver by *Plasmodium* sporozoites is slowed, reduced, or prevented. Pharmaceutical compositions comprise a pharmaceutically acceptable vehicle. Descriptions of suitable pharmaceutically acceptable vehicles, and factors involved in their selection, are found in a variety of readily available sources.

Administration typically is parenteral. Pharmaceutical compositions suitable for parenteral administration comprise various aqueous media such as aqueous dextrose and saline solutions and glycol solutions, and may comprise suitable stabilizing and/or buffering agents. In some variations, 5D5 antibodies are provided in a single or a multi-use vial as a lyophilized sterile powder, under vacuum. Packages or kits containing such vials may also include one or more vials of Bacteriostatic Water for Injection (BWFI), USP, which may contain a preservative (e.g. benzyl alcohol).

A pharmaceutical composition comprising one or more of the 5D5 antibodies disclosed herein can be administered prophylactically to reduce or prevent cleavage of CSP and thereby slow, reduce, or prevent *Plasmodium* sporozoites from invading the liver. Such compositions can be administered to malaria-naïve individuals (e.g., military personnel, state-department personnel, travelers) entering endemic regions to reduce or prevent infection. In some variations, a pharmaceutical composition comprising a 5D5 antibody can be administered in conjunction with a vaccine composition comprising a malarial antigen such as those disclosed in Mata et al., *BioMed Research Int'l. Vol.* 2013, Article ID 282913, 2013. Unless otherwise indicated, administration "in conjunction with" a traditional malaria vaccine includes sequential administration (either before or after administration of a traditional malaria vaccine) as well as administration of a 5D5 antibody in a composition comprising an agent that raises an immune response against the *Plasmodium*.

A pharmaceutical composition comprising 5D5 antibodies can be administered to treat malaria in an individual already infected with a *Plasmodium* species. In some variations, a pharmaceutical composition comprising 5D5 antibodies is administered in conjunction with one or more other anti-malarial drugs, such as atovaquone and proguanil, chloroquine, doxycycline, mefloquine, and primaquine. Unless otherwise indicated, administration "in conjunction with" an anti-malarial drug includes sequential administration (either before or after administration of an anti-malarial drug) as well as administration of a 5D5 antibody in a composition comprising an anti-malarial drug.

The following examples are provided to illustrate certain particular features and/or embodiments. The examples should not be construed to limit the disclosure to these particular features or embodiments.

Example 1. Antibody Production and Purification

Antibodies were prepared by Precision Antibody, Inc. (Columbia, Md.). Three Balb/c mice were immunized with recombinant full-length *P. falciparum* CSP (rCSP; SEQ ID NO:8) produced by Pfenex, Inc. (San Diego, Calif.) Serum titers were determined from tail bleed samples via ELISA, and splenocytes were harvested and fused once titers exceeded 1:50,000.

Example 2. Reactivity of Anti-CSP mAbs

A panel of 14 mAbs generated as described in Example 1 were tested for binding to rCSP by biolayer interference assay (BLI), which measures changes in an interference pattern generated from visible light reflected from an optical layer and a biolayer containing a mAb for characterizing its binding profile of rCSP, and by Western blot. The results of the BLI assays are shown in FIG. 1. Most of the antibodies tested demonstrated a strong association to rCSP. Several of the antibodies demonstrated rapid dissociation from rCSP, with 5D5 being the most rapid.

Example 3. Binding of mAbs to CSP Domains

The same panel of 14 mAbs was used in an indirect ELISA to determine binding to long peptides corresponding to the N-terminal (SEQ ID NO:9), repeat (SEQ ID NO:10), and C-terminal (SEQ ID NO:11) domains of CSP. Only mAb 5D5 bound the N-terminal region of CSP (FIG. 2A), while other antibodies bound either to the repeat or C-terminal region of CSP (FIG. 2B).

Example 4. Binding of mAb 5D5 to Native CSP

An immunofluorescence assay (IFA) was used to determine if mAb 5D5 bound to native CSP. Transgenic *P. berghei* sporozoites containing a portion of the *P. falciparum* CSP (repeat region and a small portion of the N-terminal domain, including the cleavage site) were the generous gift of Dr. E. Nardin. Sporozoites were obtained by feeding *Anopheles stephensi* mosquitoes on infected Swiss-Webster mice (Taconic Laboratories) and harvesting sporozoites from dissected salivary glands 18-21 days after the last blood meal. Transgenic *P. berghei* sporozoites were air-dried onto multispot glass slides and incubated for 1 hour at room temperature with mAbs diluted in PBS+1% BSA. Slides were washed 3× in PBS, incubated for 1 hour at room temperature with a FITC-labeled goat anti-mouse IgG antibody (Kirkegaard and Perry, Gaithersburg, Md.), washed again, and then viewed under a fluorescence microscope.

*P. falciparum* 3D7 sporozoites air-dried onto multiport glass slides and were incubated for 30 min at 37° C. in a humidified chamber with mAbs diluted in PBS. Slides were washed 3× in PBS and incubated for 30 min at 37° C. in the dark with a FITC-labeled goat anti-mouse IgG antibody (Kirkegaard and Perry, Gaithersburg, Md.) diluted 1:40 in PBS containing 0.02% Evans blue. Slides were washed again, mounted with VECTASHIELD® mounting media, and viewed under an epifluorescence microscope.

A weak fluorescence signal was detected with mAb 5D5 compared with the signal generated by control mAb 2G9, which recognizes the CSP repeat region.

An IFA was also performed using a chimeric rodent malaria parasite *P. berghei* that expresses a larger portion of the N-terminal region (amino acids 22-92) of the *P. falciparum* CSP. Again, mAb 5D5 generated a weak fluorescence signal as compared to mAb 2G9. The mAb 5D5 recognized *P. falciparum* 3D7 parasites in situ but required a higher concentration compared to mAb 2G9 for a signal to be detected.

Figure 3:
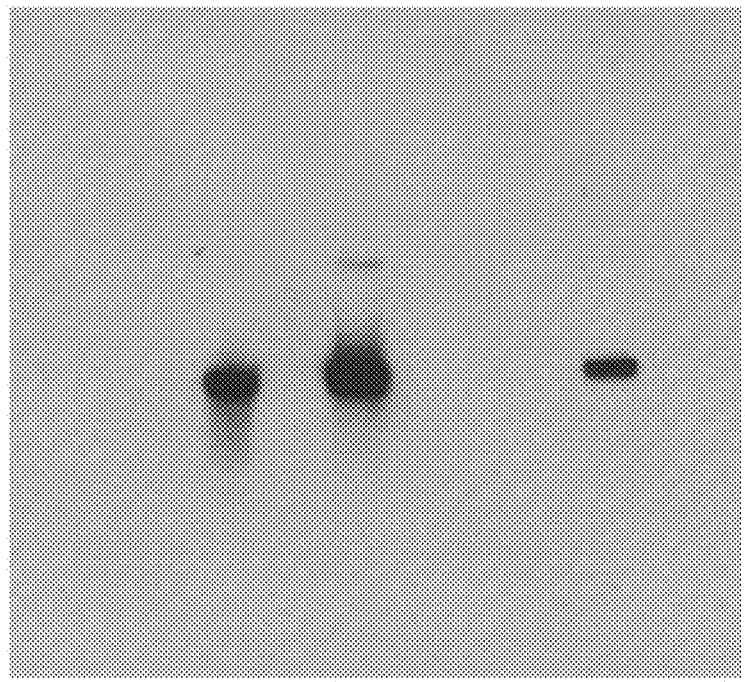
FIG. 3. Photomicrograph of Western Blot showing binding of anti-CSP mAbs 2G9 and 5D5 to P. falciparum sporozoites and rCSP under reducing conditions. Lanes 1 and 3, 25,000 P. falciparum sporozoites; lanes 2 and 4, 0.25 µg rCSP. See Example 4.

Binding to native CSP also was examined via western blot with *P. falciparum* 3D7 sporozoite lysate and rCSP under reducing conditions (FIG. 3). Differential binding was seen with the mAb 5D5, whereas the control mAb 2G9 bound to rCSP in sporozoite lysate and to rCSP.

Example 5. Peptide Mapping of Anti-CSP mAbs

To define further which area of the N-terminal region mAb 5D5 recognizes, an indirect ELISA was performed with overlapping 15-mer peptides spanning the entire CSP. This mapping was conducted by AscentGene, Rockville, Md., using peptides diluted in DMSO to a concentration of 2 µg/ml. Plates were blocked with BSA and incubated with 1.3 µg/well of each mAb. An HRP-conjugated anti-mouse secondary antibody (1:10,000) was used, followed by detection with TMB substrate.

Figures 4A, 4B, 4C:
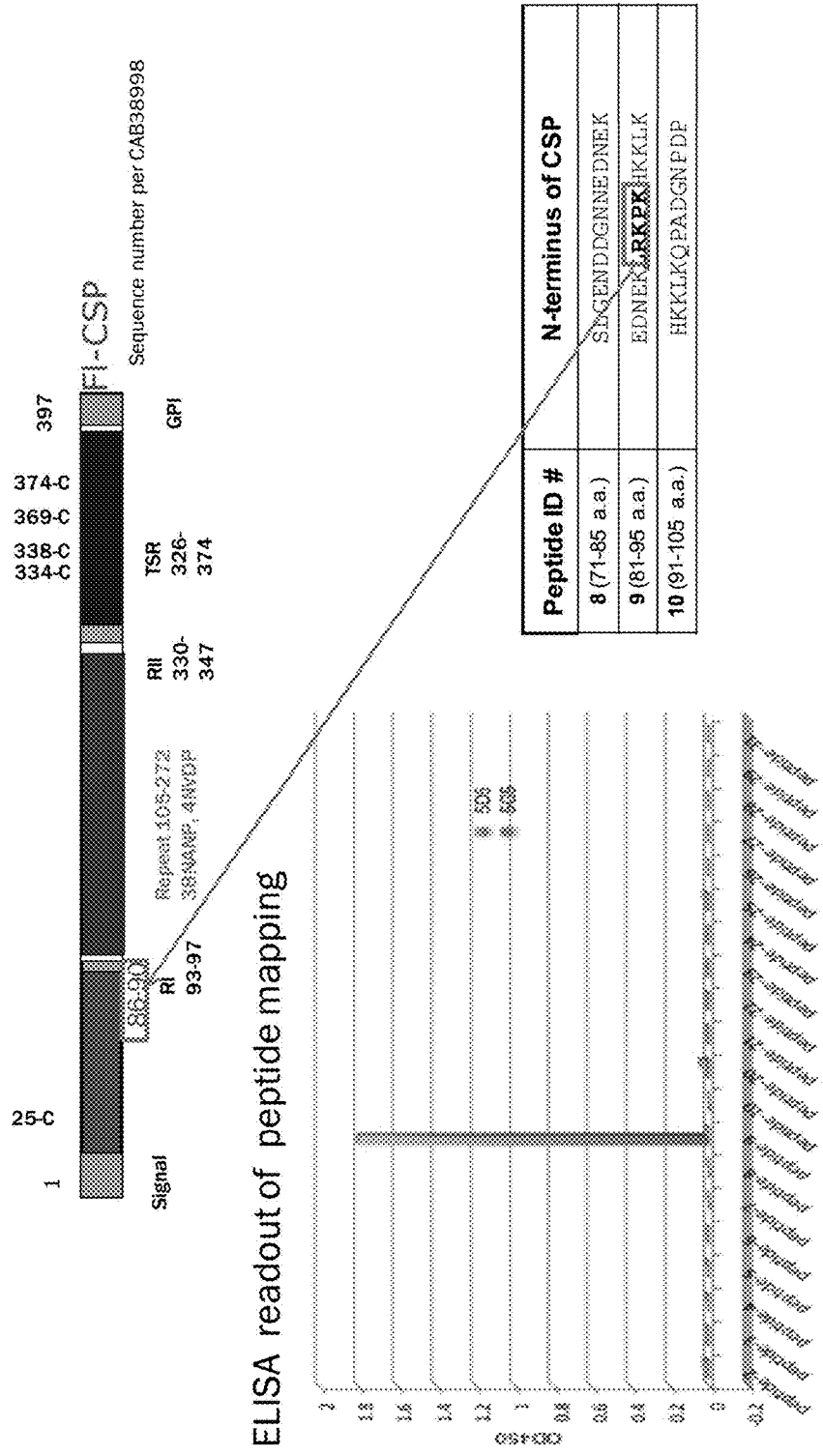
FIGS. 4A-C. Mapping of mAb 5D5 to a specific region of the N-terminal CSP domain.

The results are shown in FIG. 4C. Strong reactivity of the 5D5 mAb was found only to peptide 9 (SEQ ID NO:18), which consisted of amino acids 81-95 of CSP. No reactivity was seen with mAb 5D5 to peptide 8 (amino acids 71-85 of CSP; SEQ ID NO:17) or peptide 10 (amino acids 91-106 of CSP; SEQ ID NO:19). The putative 5D5 epitope was identified as EDNEKLRKPKHKKLK (SEQ ID NO:7).

To confirm the epitope, competitive ELISA assays were performed using a series of 9-mer peptides (peptide A, SEQ ID NO:21; peptide B, SEQ ID NO:22; peptide C, SEQ ID NO:23; peptide D, SEQ ID NO:24; peptide E, SEQ ID NO:25) encompassing the sequence corresponding to peptides 8-10 to identify which peptides competed with rCSP for binding to mAb 5D5. The results are shown in Table 1. The results confirm that peptide 9 competes with rCSP for binding to mAb 5D5.

TABLE 1

| Peptide concen-tration | A | B | C | D | E | 8 | 9 | 10 | rCSP |
|---|---|---|---|---|---|---|---|---|---|
| 0.01 µg/ml | 3.570 | 3.510 | 3.488 | 3.453 | 3.392 | 3.353 | 0.246 | 3.336 | 0.340 |
| 0.001 µg/ml | 1.052 | 1.026 | 0.976 | 0.989 | 0.925 | 0.952 | 0.190 | 0.920 | 0.191 |
| NC | 0.245 | 0.204 | 0.230 | 0.226 | 0.211 | 0.219 | 0.229 | 0.211 | 0.198 |
| PC 0.01 µg/ml | 3.595 | 3.405 | 3.557 | 3.506 | 3.471 | 3.417 | 3.442 | 3.393 | 3.490 |
| PC 0.001 µg/ml | 1.352 | 1.315 | 1.311 | 1.304 | 1.228 | 1.212 | 1.208 | 1.168 | 1.174 |

Example 6. Passive Transfer of Anti-CSP mAb Decreases Parasite Liver Load

Challenge studies were performed with C57Bl/6 mice and live chimeric *P. berghei* sporozoites expressing either the repeat region (and a small portion of the N-terminal domain) or the majority of the N terminal domain of *P. falciparum*, both of which contain the cleavage site and the 5D5 epitope. Each mouse was injected intravenously with 300 µg of mAb 5D5 or one of the positive control mAbs 3D11 or 2A10 in PBS just before challenge with 10,000 sporozoites suspended in 100 µl of PBS containing 1% normal mouse serum. Mice were euthanized 40-42 hours post challenge, and their livers were excised. Total RNA was extracted from the livers and used to estimate liver parasite load by real time PCR as described in Bruna-Romero et al., *Int J. Parasitol.* 31, 1499, 2001.

Figure 5:
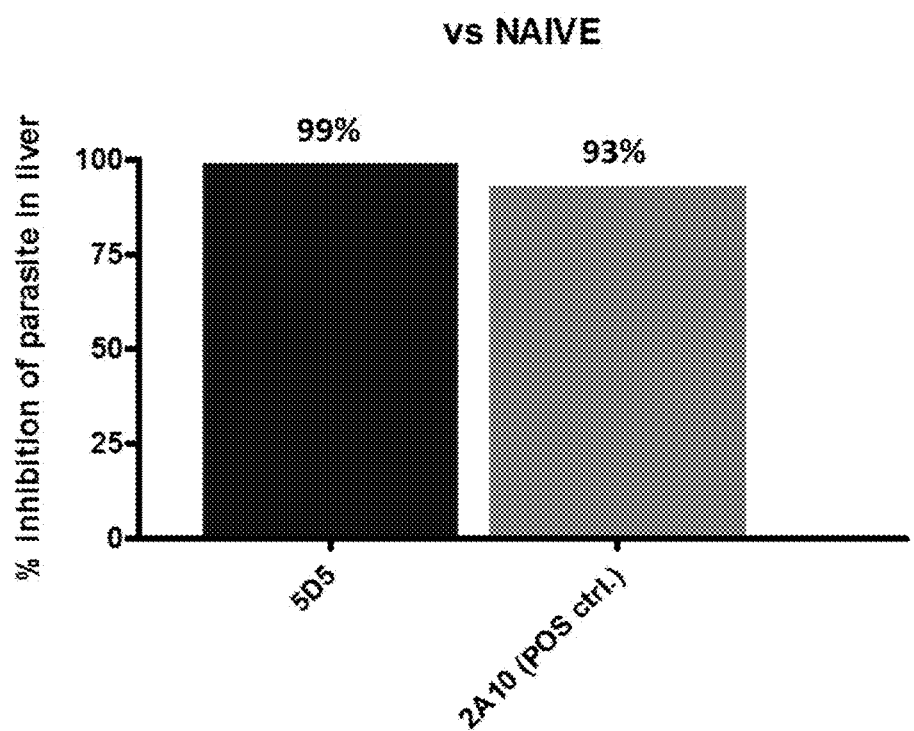
FIG. 5. Graph showing percent inhibition by 1 µg/ml of mAb 5D5 and control mAb 2A10 of parasites in the liver of mice challenged with transgenic P. berghei sporozoites containing a portion of the P. falciparum CSP (repeat region and a small portion of the N-terminal domain, including the cleavage site). See Example 6.

The results are shown in FIG. 5. Liver load of parasites in mice to which mAb 5D5 was administered was significantly decreased compared to the naïve control group.

Example 7. Analysis of mAb 5D5 Heavy and Light Chains

Total RNA Extraction.

Total RNA was extracted from hybridoma cells using Trizol Reagent (Invitrogen Catalog Number 15596) and prepared according to the manufacturer's protocol. Isopropanol-precipitated RNA was resuspended in sterile RNAse/DNAse free $H_2O$ and the absorbance at A260 determined. Electrophoresis on a 1% TAE-agarose gel was used to determine quality.

First-Round RT-PCR.

5 µg of RNA was used for the first strand cDNA preparation using SUPERSCRIPT® III (Invitrogen catalog #18080-051). Oligo-dT was used as primer. cDNA was purified using Qiagen QIAQUICK® columns and tailed using terminal deoxyribonucleotide transferase (Invitrogen catalog #10533-065). The polyadenylated first strand cDNA was purified using Qiagen QIAQUICK® columns as before. PCR was performed with reverse primers specific for the heavy and light chains and with a common oligodT primer as a forward primer. Reverse primers were located in the constant regions of heavy and light chains. No restriction sites were engineered into the primers.

PCR Conditions:

| | | |
|---|---|---|
| i. | Forward primer only: | 50° C., 5 cycles |
| ii. | Add reverse primer(s) | |
| iii. | Denaturation step | 94° C., 120 seconds |
| iv. | 35 Cycles of: | 94° C., 30 seconds |
| | | 55° C., 30 seconds |
| | | 72° C., 120 seconds |

Analysis of PCR Results.

PCR reaction samples were analyzed on a preparative TAE-1% agarose gel to visualize the amplified DNA fragments. The correct antibody variable region DNA fragments should have a size between 600-750 base pairs. The amplified PCR products are excised from the gel and purified using Qiagen QIAQUICK® columns.

The purified PCR products were ligated into EcoRV-digested pBluescript using a QUICK-LIGATION® kit (New England BioLabs, Inc. Catalog #M2200S) and transformed into *E. coli* strain DH5-α on X-Gal/IPTG LB plates. The next day, white colonies were placed into 3 ml of LB+amp broth, grown overnight, and purified using Qiagen minicolumns, followed by restriction digestions and gel electrophoresis. A minimum of 6 correctly sized clones of each light and heavy chain were sequenced.

Sequencing.

The cloned DNAs were sequenced by Sequetech (Mountain View, Calif.) using an ABI 3730XL Capillary Sequencer using primers which flank both ends of the cDNA insert. The resulting DNA files were assembled and edited using VECTOR NTI®. The resulting assemblies translated to provide a deduced amino acid sequence.

The heavy chain insert encodes an $IgG_1$ isotype murine antibody. Full-length clones included a 51 bp 5' untranslated leader preceding a canonical 19 amino acid signal sequence. The light chain insert encodes an kappa isotype murine antibody. Full-length clones included a 27 bp 5' untranslated leader preceding a canonical 20 amino acid signal sequence.

The amino acid sequences of the heavy and light chains are shown in FIG. 6A and FIG. 6B. The CDRs of mAb 5D5 were identified using the Kabat database (bioinf<dot>org<dot>uk<forward slash>abs<forward slash>#cdrdef); see "Protein Sequence and Structure Analysis of Antibody Variable Domains" in *Antibody Engineering Lab Manual*, Dübel & Kontermann, eds., Springer-Verlag, Heidelberg, 2001).

The invention claimed is:

1. A cDNA molecule comprising a coding sequence for a variable region of a heavy chain of an antibody, wherein the variable region comprises:
   (i) a first heavy chain complementarity determining region ($CDR_H$) comprising the amino acid sequence SEQ ID NO:1; a second $CDR_H$ comprising the amino acid sequence SEQ ID NO:2; and a third $CDR_H$ comprising the amino acid sequence SEQ ID NO:3; or
   (ii) the complementarity determining regions of the heavy chain variable region of the antibody deposited under Accession No. MRA-1242.

2. The cDNA molecule of claim 1, wherein the variable region comprises the first $CDR_H$ comprising the amino acid sequence SEQ ID NO:1; the second $CDR_H$ comprising the amino acid sequence SEQ ID NO:2; and the third $CDR_H$ comprising the amino acid sequence SEQ ID NO:3.

3. The cDNA molecule of claim 1, wherein the variable region comprises the complementarity determining regions of the heavy chain of the antibody deposited under Accession No. MRA-1242.

4. A cDNA molecule, comprising a coding sequence for a variable region of a light chain of an antibody, wherein the variable region comprises:
   (i) a first $CDR_L$ comprising the amino acid sequence SEQ ID NO:4; a second $CDR_L$ comprising the amino acid sequence SEQ ID NO:5; and a third $CDR_L$ comprising the amino acid sequence SEQ ID NO:6; or
   (ii) the complementarity determining regions of the light chain variable region of the antibody deposited under Accession No. MRA-1242.

5. The cDNA molecule of claim 4, wherein the light chain variable region comprises the first $CDR_L$ comprising the amino acid sequence SEQ ID NO:4; the second $CDR_L$ comprising the amino acid sequence SEQ ID NO:5; and the third $CDR_L$ comprising the amino acid sequence SEQ ID NO:6.

6. The cDNA molecule of claim 4, wherein the light chain variable region comprises the complementarity determining regions of the light chain of the antibody deposited under Accession No. MRA-1242.

7. The cDNA molecule of claim 3, further comprising a coding sequence for a light chain variable region comprising the complementarity determining regions of the antibody deposited under Accession No. MRA-1242.

* * * * *

SEQUENCE LISTING

```
<160> NUMBER OF SEQ ID NOS: 25

<210> SEQ ID NO 1
<211> LENGTH: 10
<212> TYPE: PRT
<213> ORGANISM: Mus musculus

<400> SEQUENCE: 1

Gly Tyr Thr Phe Thr Gly Tyr Gly Leu Ser
1               5                   10

<210> SEQ ID NO 2
<211> LENGTH: 19
<212> TYPE: PRT
<213> ORGANISM: Mus musculus

<400> SEQUENCE: 2
```

```
Ile Tyr Pro Arg Ser Gly Asn Thr Tyr Tyr Asn Glu Lys Phe Lys Gly
 1               5                   10                  15

Lys Ala Thr

<210> SEQ ID NO 3
<211> LENGTH: 9
<212> TYPE: PRT
<213> ORGANISM: Mus musculum

<400> SEQUENCE: 3

Ser Trp Gly Asn Ser Ser Phe Val Tyr
 1               5

<210> SEQ ID NO 4
<211> LENGTH: 11
<212> TYPE: PRT
<213> ORGANISM: Mus musculum

<400> SEQUENCE: 4

Lys Ala Ser Gln Ser Val Thr Asn Asp Val Thr
 1               5                   10

<210> SEQ ID NO 5
<211> LENGTH: 7
<212> TYPE: PRT
<213> ORGANISM: Mus musculum

<400> SEQUENCE: 5

Ala Ser Asn Arg Tyr Thr Gly
 1               5

<210> SEQ ID NO 6
<211> LENGTH: 9
<212> TYPE: PRT
<213> ORGANISM: Mus musculum

<400> SEQUENCE: 6

Gln Gln Asp Tyr Ser Ser Pro Phe Thr
 1               5

<210> SEQ ID NO 7
<211> LENGTH: 15
<212> TYPE: PRT
<213> ORGANISM: Plasmodium falciparum

<400> SEQUENCE: 7

Glu Gln Asn Glu Lys Leu Arg Lys Pro Lys His Lys Lys Leu Lys
 1               5                   10                  15

<210> SEQ ID NO 8
<211> LENGTH: 397
<212> TYPE: PRT
<213> ORGANISM: Plasmodium falciparum

<400> SEQUENCE: 8

Met Met Arg Lys Leu Ala Ile Leu Ser Val Ser Ser Phe Leu Phe Val
 1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Thr Asn Leu Tyr
            35                  40                  45

Asn Glu Leu Glu Met Asn Tyr Tyr Gly Lys Gln Glu Asn Trp Tyr Ser
50                  55                  60
```

Leu Lys Lys Asn Ser Arg Ser Leu Gly Glu Asn Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
            115                 120                 125

Asn Ala Asn Pro Asn Ala Asn Pro Asn Ala Asn Pro Asn Ala Asn Pro
            130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
            165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
            195                 200                 205

Asn Ala Asn Pro Asn Ala Asn Pro Asn Ala Asn Pro Asn Ala Asn Pro
210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
            245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
            275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
            325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
            355                 360                 365

Cys Lys Met Glu Lys Cys Ser Ser Val Phe Asn Val Val Asn Ser Ser
            370                 375                 380

Ile Gly Leu Ile Met Val Leu Ser Phe Leu Phe Leu Asn
385                 390                 395

<210> SEQ ID NO 9
<211> LENGTH: 81
<212> TYPE: PRT
<213> ORGANISM: Plasmodium falciparum

<400> SEQUENCE: 9

Tyr Gly Ser Ser Ser Asn Thr Arg Val Leu Asn Glu Leu Asn Tyr Asp
1               5                   10                  15

Asn Ala Gly Thr Asn Leu Tyr Asn Glu Leu Glu Met Asn Tyr Tyr Gly
            20                  25                  30

Lys Gln Glu Asn Trp Tyr Ser Leu Lys Lys Asn Ser Arg Ser Leu Gly

```
                            35                  40                  45

Glu Asn Asp Asp Gly Asn Asn Glu Asp Asn Glu Lys Leu Arg Lys Pro
         50                  55                  60

Lys His Lys Lys Leu Lys Gln Pro Ala Asp Gly His His His His
 65                  70                  75                  80

His
```

```
<210> SEQ ID NO 10
<211> LENGTH: 23
<212> TYPE: PRT
<213> ORGANISM: Plasmodium falciparum

<400> SEQUENCE: 10

Cys Asn Val Asp Pro Asn Ala Asn Pro Asn Val Asp Pro Asn Ala Asn
  1               5                  10                  15

Pro Asn Ala Asn Pro Asn Ala
            20
```

```
<210> SEQ ID NO 11
<211> LENGTH: 57
<212> TYPE: PRT
<213> ORGANISM: Plasmodium falciparum

<400> SEQUENCE: 11

Gly Ile Gln Val Arg Ile Lys Pro Gly Ser Ala Asn Lys Pro Lys Asp
  1               5                  10                  15

Glu Leu Asp Tyr Ala Asn Asp Ile Glu Lys Lys Ile Ser Lys Met Glu
             20                  25                  30

Lys Cys Ser Ser Val Phe Asn Val Val Asn Ser Ser Ile Gly Leu Ile
         35                  40                  45

Met Val Leu Ser Phe Leu Phe Leu Asn
         50                  55
```

```
<210> SEQ ID NO 12
<211> LENGTH: 23
<212> TYPE: PRT
<213> ORGANISM: Plasmodium falciparum

<400> SEQUENCE: 12

Asp Gly Asn Asn Glu Asp Asn Glu Lys Leu Arg Lys Pro Lys His Lys
  1               5                  10                  15

Lys Leu Lys Gln Pro Ala Asp
            20
```

```
<210> SEQ ID NO 13
<211> LENGTH: 617
<212> TYPE: DNA
<213> ORGANISM: Plasmodium falciparum

<400> SEQUENCE: 13
gaattctttt ttttttttt tttttgaac ctatgatcaa tgtcttcttc acagtccctg      60
aacacactga ctctaaccat ggaatggatc tggatctttc tcttcatcct gtcaggaact    120
gcaggtgtcc aatcccaggt tcacctgcag cagtctggag gtgaggtggc gaggcctggg    180
gcttcagtga agctgtcctg caaggcttct ggctacacct tcacaggcta tggtctaagc    240
tgggtgaagc agagaactgg acagggcctt gagtggattg agagattta tcctagaagt    300 ggtaatactt actacaatga aagttcaag ggcaaggcca cactgactgc agacaaatcc    360
tccagcacag cgtacatgga gctccgcagc ctgacatctg aggactctgc ggtctatttc    420
```

```
tgtgcaagat cgtggggtaa ctcctcgttt gtttactggg gccaagggac tctggtcact    480
gtctctgcag ccaaaacgac accccatct gtctatccac tggcccctgg atctgctgcc     540
caaactaact ccatggtgac cctgggatgc ctggtcaagg ctatttccc tgagccagtg     600 acagtgacct ggaactc                                                   617
```

<210> SEQ ID NO 14
<211> LENGTH: 179
<212> TYPE: PRT
<213> ORGANISM: Plasmodium falciparum

<400> SEQUENCE: 14

```
Met Glu Trp Ile Trp Ile Phe Leu Phe Ile Leu Ser Gly Thr Ala Gly
 1               5                  10                  15

Val Gln Ser Gln Val His Leu Gln Gln Ser Gly Gly Glu Val Ala Arg
             20                  25                  30

Pro Gly Ala Ser Val Lys Leu Ser Cys Lys Ala Ser Gly Tyr Thr Phe
         35                  40                  45

Thr Gly Tyr Gly Leu Ser Trp Val Lys Gln Arg Thr Gly Gln Gly Leu
     50                  55                  60

Glu Trp Ile Gly Glu Ile Tyr Pro Arg Ser Gly Asn Thr Tyr Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met Glu Leu Arg Ser Leu Thr Ser Glu Asp Ser Ala Val
            100                 105                 110

Tyr Phe Cys Ala Arg Ser Trp Gly Asn Ser Ser Phe Val Tyr Trp Gly
        115                 120                 125

Gln Gly Thr Leu Val Thr Val Ser Ala Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn
```

<210> SEQ ID NO 15
<211> LENGTH: 461
<212> TYPE: DNA
<213> ORGANISM: Plasmodium falciparum

<400> SEQUENCE: 15

```
atacatcagg caggcaaggg catcaagatg aagtcacaga cccaggtctt cgtatttcta    60
ctgctctgtg tgtctggtgc tcatgggagt attgtgatga cccagactcc caaattcctg   120
cttgtatcag caggagacag ggttaccata acctgcaagg ccagtcagag tgtgactaat   180
gatgtaactt ggtaccaaca gaagccaggg cagtctccta aactgctgat atactatgca   240
tccaatcgct acactggagt ccctgatcgc ttcactggca gtggatatgg gacggatttc   300
actttcacca tcagcactgt gcaggctgaa gacctggcag tttatttctg tcagcaggat   360
tatagctctc cattcacgtt cggctcgggg acaaagttgg aaataaaacg ggctgatgct   420
gcaccaactg tatccatctt cccaccatcc agtgagcagt t                        461
```

<210> SEQ ID NO 16
<211> LENGTH: 151

```
<212> TYPE: PRT
<213> ORGANISM: Plasmodium falciparum

<400> SEQUENCE: 16

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
                20                  25                  30

Val Ser Ala Gly Asp Arg Val Thr Ile Thr Cys Lys Ala Ser Gln Ser
            35                  40                  45

Val Thr Asn Asp Val Thr Trp Tyr Gln Gln Lys Pro Gly Gln Ser Pro
        50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Phe Thr Phe Gly Ser Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Ser Asn Ser Cys Ser Pro
145                 150

<210> SEQ ID NO 17
<211> LENGTH: 15
<212> TYPE: PRT
<213> ORGANISM: Plasmodium falciparum

<400> SEQUENCE: 17

Ser Leu Gly Glu Asn Asp Asp Gly Asn Asn Glu Asp Asn Glu Lys
1               5                   10                  15

<210> SEQ ID NO 18
<211> LENGTH: 15
<212> TYPE: PRT
<213> ORGANISM: Plasmodium falciparum

<400> SEQUENCE: 18

Glu Asp Asn Glu Lys Leu Arg Lys Pro Lys His Lys Lys Leu Lys
1               5                   10                  15

<210> SEQ ID NO 19
<211> LENGTH: 14
<212> TYPE: PRT
<213> ORGANISM: Plasmodium falciparum

<400> SEQUENCE: 19

His Lys Lys Leu Lys Gln Pro Ala Asp Gly Asn Pro Asp Pro
1               5                   10

<210> SEQ ID NO 20
<211> LENGTH: 5
<212> TYPE: PRT
<213> ORGANISM: Plasmodium falciparum

<400> SEQUENCE: 20

Lys Leu Lys Gln Pro
1               5
```

```
<210> SEQ ID NO 21
<211> LENGTH: 9
<212> TYPE: PRT
<213> ORGANISM: Plasmodium falciparum

<400> SEQUENCE: 21

Asp Gly Asn Asn Glu Asp Asn Glu Lys
 1               5

<210> SEQ ID NO 22
<211> LENGTH: 9
<212> TYPE: PRT
<213> ORGANISM: Plasmodium falciparum

<400> SEQUENCE: 22

Asn Glu Asp Asn Glu Lys Leu Arg Lys
 1               5

<210> SEQ ID NO 23
<211> LENGTH: 10
<212> TYPE: PRT
<213> ORGANISM: Plasmodium falciparum

<400> SEQUENCE: 23

Asn Glu Lys Leu Arg Lys Pro Lys His Lys
 1               5                  10

<210> SEQ ID NO 24
<211> LENGTH: 11
<212> TYPE: PRT
<213> ORGANISM: Plasmodium falciparum

<400> SEQUENCE: 24

Leu Arg Lys Pro Lys His Lys Lys Leu Lys Gln
 1               5                  10

<210> SEQ ID NO 25
<211> LENGTH: 11
<212> TYPE: PRT
<213> ORGANISM: Plasmodium falciparum

<400> SEQUENCE: 25

Pro Lys His Lys Lys Leu Lys Gln Pro Ala Asp
 1               5                  10
```